United States Patent
Karmarkar

(10) Patent No.: US 8,509,876 B2
(45) Date of Patent: Aug. 13, 2013

(54) IMPLANTABLE MRI COMPATIBLE STIMULATION LEADS AND ANTENNAS AND RELATED SYSTEMS AND METHODS

(75) Inventor: Parag V. Karmarkar, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 1772 days.

(21) Appl. No.: 11/573,226

(22) PCT Filed: Aug. 9, 2005

(86) PCT No.: PCT/US2005/028116
§ 371 (c)(1),
(2), (4) Date: Aug. 6, 2007

(87) PCT Pub. No.: WO2006/031317
PCT Pub. Date: Mar. 23, 2006

(65) Prior Publication Data
US 2008/0039709 A1    Feb. 14, 2008

Related U.S. Application Data

(60) Provisional application No. 60/600,020, filed on Aug. 9, 2004, provisional application No. 60/608,195, filed on Sep. 9, 2004.

(51) Int. Cl.
*A61B 5/055*    (2006.01)
(52) U.S. Cl.
USPC ........... 600/424; 600/407; 600/410; 324/318; 324/322

(58) Field of Classification Search
USPC ................... 600/424; 324/318, 322; 606/41
See application file for complete search history.

(56) References Cited

U.S. PATENT DOCUMENTS

| | | | |
|---|---|---|---|
| 5,246,438 A | 9/1993 | Langberg | |
| 5,523,534 A | 6/1996 | Meister | |
| 6,100,695 A * | 8/2000 | DeMeester et al. | 324/318 |
| 6,246,898 B1 * | 6/2001 | Vesely et al. | 600/424 |
| 6,284,971 B1 | 9/2001 | Atalar et al. | |
| 6,400,976 B1 | 6/2002 | Champeau | |
| 6,567,690 B2 | 5/2003 | Giller et al. | |
| 6,765,779 B2 | 7/2004 | Stevenson et al. | |
| 6,765,780 B2 | 7/2004 | Brendel | |

(Continued)

FOREIGN PATENT DOCUMENTS

| WO | 02083016 A1 | 10/2002 |
|---|---|---|
| WO | 2004095385 82 | 11/2004 |

(Continued)

OTHER PUBLICATIONS

International Search Report mailed Apr. 21, 2006 for corresponding PCT application No. PCTUS05/28116 (8 pages).

*Primary Examiner* — Baisakhi Roy
(74) *Attorney, Agent, or Firm* — Frommer Lawrence & Haug LLP; Bruce E. Black

(57) ABSTRACT

In vivo medical stimulation probes include an elongate lead having at least one stimulation electrode disposed on a distal portion thereof. The probes may include a plurality of axially spaced apart RF chokes disposed on and/or in an axially extending shielding layer of the lead in advance of the at least one electrode to inhibit induced RF current from forming and/or traveling along the shielding layer.

65 Claims, 12 Drawing Sheets

(56) References Cited

U.S. PATENT DOCUMENTS

| | | | |
|---|---|---|---|
| 6,888,715 B2 | 5/2005 | Stevenson et al. | |
| 6,987,660 B2 | 1/2006 | Stevenson et al. | |
| 7,012,192 B2 | 3/2006 | Stevenson et al. | |
| 7,035,077 B2 | 4/2006 | Brendel | |
| 7,038,900 B2 | 5/2006 | Stevenson et al. | |
| 7,136,273 B2 | 11/2006 | Stevenson et al. | |
| 7,310,216 B2 | 12/2007 | Stevenson et al. | |
| 7,387,628 B1 * | 6/2008 | Behl et al. | 606/41 |
| 7,489,495 B2 | 2/2009 | Stevenson | |
| 7,535,693 B2 | 5/2009 | Stevenson et al. | |
| 7,602,187 B2 * | 10/2009 | Luedeke et al. | 324/318 |
| 7,623,335 B2 | 11/2009 | Stevenson et al. | |
| 7,689,288 B2 | 3/2010 | Stevenson et al. | |
| 7,751,903 B2 | 7/2010 | Stevenson et al. | |
| 7,765,005 B2 | 7/2010 | Stevenson | |
| 7,787,958 B2 | 8/2010 | Stevenson | |
| 7,822,460 B2 | 10/2010 | Halperin et al. | |
| 7,844,319 B2 * | 11/2010 | Susil et al. | 600/411 |
| 7,853,325 B2 | 12/2010 | Dabney et al. | |
| 7,899,551 B2 * | 3/2011 | Westlund et al. | 607/122 |
| 7,916,013 B2 | 3/2011 | Stevenson | |
| 7,917,219 B2 | 3/2011 | Stevenson et al. | |
| RE42,856 E * | 10/2011 | Karmarkar et al. | 600/423 |
| 8,108,028 B2 * | 1/2012 | Karmarkar | 600/423 |
| 8,433,421 B2 * | 4/2013 | Atalar et al. | 607/63 |
| 2002/0161403 A1 | 10/2002 | Meadows et al. | |
| 2003/0050557 A1 * | 3/2003 | Susil et al. | 600/424 |
| 2003/0179536 A1 | 9/2003 | Stevenson et al. | |
| 2003/0213604 A1 | 11/2003 | Stevenson et al. | |
| 2003/0213605 A1 | 11/2003 | Brendel et al. | |
| 2004/0006274 A1 | 1/2004 | Giller et al. | |
| 2004/0046557 A1 | 3/2004 | Karmarkar et al. | |
| 2004/0049121 A1 | 3/2004 | Yaron | |
| 2004/0133118 A1 | 7/2004 | Llinas | |
| 2004/0138518 A1 | 7/2004 | Rise et al. | |
| 2004/0181215 A1 * | 9/2004 | Kelly et al. | 606/41 |
| 2004/0201947 A1 | 10/2004 | Stevenson et al. | |
| 2004/0257747 A1 | 12/2004 | Stevenson et al. | |
| 2004/0263174 A1 * | 12/2004 | Gray et al. | 324/322 |
| 2005/0007718 A1 | 1/2005 | Stevenson et al. | |
| 2005/0190527 A1 | 9/2005 | Stevenson et al. | |
| 2005/0201039 A1 | 9/2005 | Stevenson et al. | |
| 2005/0219787 A1 | 10/2005 | Stevenson et al. | |
| 2005/0247475 A1 | 11/2005 | Stevenson et al. | |
| 2005/0248907 A1 | 11/2005 | Stevenson et al. | |
| 2006/0028784 A1 | 2/2006 | Brendel | |
| 2006/0085043 A1 | 4/2006 | Stevenson | |
| 2006/0100506 A1 * | 5/2006 | Halperin et al. | 600/424 |
| 2006/0212096 A1 | 9/2006 | Stevenson | |
| 2006/0221543 A1 | 10/2006 | Stevenson et al. | |
| 2007/0019362 A1 | 1/2007 | Stevenson et al. | |
| 2007/0288058 A1 | 12/2007 | Halperin et al. | |
| 2008/0049376 A1 | 2/2008 | Stevenson et al. | |
| 2008/0065181 A1 | 3/2008 | Stevenson | |
| 2008/0116997 A1 | 5/2008 | Dabney et al. | |
| 2008/0119919 A1 * | 5/2008 | Atalar et al. | 607/116 |
| 2008/0132987 A1 | 6/2008 | Westlund et al. | |
| 2008/0269591 A1 | 10/2008 | Halperine et al. | |
| 2009/0116167 A1 | 5/2009 | Stevenson et al. | |
| 2009/0259265 A1 | 10/2009 | Stevenson et al. | |
| 2010/0016936 A1 | 1/2010 | Stevenson et al. | |
| 2010/0023000 A1 | 1/2010 | Stevenson et al. | |
| 2010/0023095 A1 | 1/2010 | Stevenson et al. | |
| 2010/0160997 A1 | 6/2010 | Johnson et al. | |
| 2010/0168821 A1 | 7/2010 | Johnson et al. | |
| 2010/0174349 A1 | 7/2010 | Stevenson et al. | |
| 2010/0191236 A1 | 7/2010 | Johnson et al. | |
| 2010/0198312 A1 | 8/2010 | Stevenson et al. | |
| 2010/0217262 A1 | 8/2010 | Stevenson et al. | |
| 2010/0222857 A1 | 9/2010 | Halperin et al. | |
| 2010/0280584 A1 | 11/2010 | Johnson et al. | |
| 2010/0321163 A1 | 12/2010 | Stevenson | |
| 2010/0324639 A1 | 12/2010 | Stevenson et al. | |
| 2011/0022140 A1 | 1/2011 | Stevenson et al. | |
| 2011/0040343 A1 | 2/2011 | Johnson et al. | |
| 2011/0054582 A1 | 3/2011 | Dabney et al. | |

FOREIGN PATENT DOCUMENTS

| | | |
|---|---|---|
| WO | WO 2004095281 A2 | 11/2004 |
| WO | WO 2005114685 A1 | 12/2005 |
| WO | 2006119492 A2 | 11/2006 |

\* cited by examiner

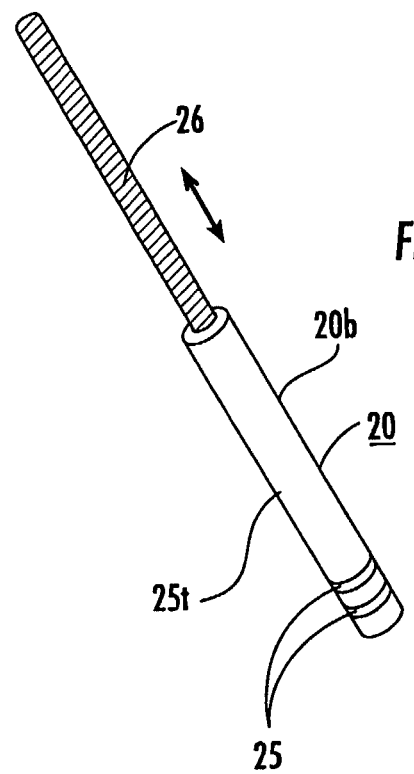
FIG. 5A
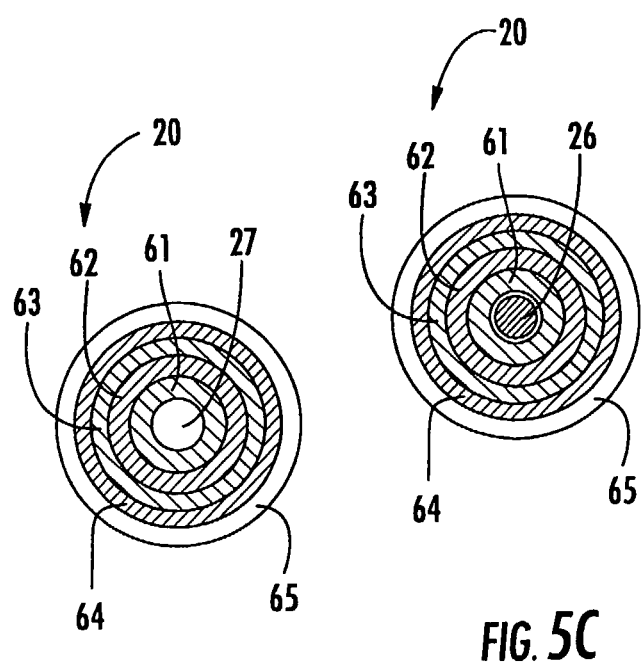
FIG. 5B
FIG. 5C

IMPLANTABLE MRI COMPATIBLE STIMULATION LEADS AND ANTENNAS AND RELATED SYSTEMS AND METHODS

RELATED APPLICATIONS

This application claims the benefit of priority to U.S. Provisional Application Ser. No. 60/600,020 filed Aug. 9, 2004 and 60/608,195, filed Sep. 9, 2004, the contents of which are hereby incorporated by reference as if recited in full herein.

GOVERNMENT FUNDING

This invention was made, in part, with United States government support under grant number HL57483 from the National Institutes of Health. The United States government has certain rights to this invention.

FIELD OF THE INVENTION

The present invention relates to interventional medical leads and may be particularly suitable for MRI compatible implantable Deep Brain Stimulation ("DBS") and/or implantable sympathetic nerve chain stimulation leads.

BACKGROUND OF THE INVENTION

Deep Brain Stimulation (DBS) is becoming an acceptable therapeutic modality in neurosurgical treatment of patients suffering from chronic pain, Parkinson's disease or seizure, and other medical conditions. Other electro-stimulation therapies have also been carried out or proposed using internal stimulation of the sympathetic nerve chain and/or spinal cord, etc.

One example of a prior art DBS system is the Activa® system from Medtronic, Inc. The Activa® system includes an implantable pulse generator stimulator that is positioned in the chest cavity of the patient and a lead with axially spaced apart electrodes that is implanted with the electrodes disposed in neural tissue. The lead is tunneled subsurface from the brain to the chest cavity connecting the electrodes with the pulse generator. These leads can have multiple exposed electrodes at the distal end that are connected to conductors which run along the length of the lead and connect to the pulse generator placed in the chest cavity.

Functional MRI is an imaging modality that can be used to evaluate cardiac, neurological and/or other disorders. It may be desirable to use MRI for patients with implanted stimulation devices and leads. However, currently available lead systems may be unsuitable to use in a magnetic resonance imaging (MRI) environment. For example, the devices may not be MRI compatible, i.e., they may contain ferromagnetic materials, which may distort the MRI images. Also, currently available lead/probe/cable systems may be susceptible to unwanted induced RF and/or AC current and/or localized heating of the tissue. For example the Medtronic Activa® device recommends that MRI imaging be carried out in a 1.5 T magnet without using body coils, i.e., only using head coils for transmission of the RF excitation pulse(s). Also, the problem of unwanted RF deposition may increase as higher magnetic fields, such as 3 T systems, become more common for MRI imaging (the RF pulses having shorter wavelengths).

It is believed that the clinical outcome of certain medical procedures, particularly those using DBS, may depend on the precise location of the electrodes that are in contact with the tissue of interest. For example, presently, to treat Parkinson's tremor, the DBS probes are placed in neural tissue with the electrodes transmitting a signal to the thalamus region of the brain. However, it has been reported that in about 30% of the patients implanted with these devices, the clinical efficacy of the device/procedure is less than optimum. This may be attributed to the inaccurate/imprecise placement of the lead/probe/electrode with respect to the cranial or neural tissue.

Other non-MRI applications, such as RF/microwave diathermy treatment, can use leads that employ an alternating current to cauterize tissue. The diathermy alternating current delivered during the therapy can be in the range of between about 1 KHz-350 MHz. In certain situations, the lead system may undesirably act as an antenna, picking-up and depositing current in localized tissue where the leads are exposed, thereby potentially increasing the SAR or specific absorption rate (a way of measuring the quantity of radiofrequency (RF) energy that is absorbed by the body).

Notwithstanding the above, there remains a need for alternative medical lead configurations.

SUMMARY OF EMBODIMENTS OF THE INVENTION

Some embodiments of the present invention provide therapeutic lead systems. The lead systems may include RF chokes and/or induced current resistant leads. The lead systems may be implantable, MRI compatible multi-purpose lead systems configured to provide an internal MRI receive antenna and at least one stimulating electrode.

The lead can be a relatively long implantable lead having a length in the body of greater than 10 cm. The at least one electrode can be a plurality of electrodes with at least one being a recording and/or a recording and stimulating and/or ablating electrode.

The device can be a multi-purpose lead system that allows for increased precision placement using an integrated MRI receive antenna and stimulation using electrodes. The lead system can have opposing distal and proximal portions with the proximal portion configured to reside external of the subject during lead placement. In some embodiments, the proximal portion can releaseably attach to either and MRI interface or an implantable pulse generator. The proximal portion can merge into a connector. The distal portion comprises a plurality of stimulating electrodes and an MRI antenna.

Certain embodiments are directed to in vivo medical stimulation probes that include: (a) an elongate lead having at least one stimulation electrode disposed on a distal portion thereof; and (b) a plurality of axially spaced apart RF chokes disposed on and/or in an axially extending shielding layer of the lead in advance of the at least one electrode to inhibit induced RF current from forming and/or traveling along the shielding layer.

The lead may be a flexible lead and the at least one electrode can be a plurality of spaced apart electrodes. The lead can include a plurality of conductors held in a core of the lead, a respective one for each electrode. The shielding layer can be discontinuous and can be configured to surround the conductors over at least a major length of the lead and terminate at a lead location that is in advance of the electrodes. The probe can include an axially extending primary inner shield surrounding the core with the plurality of electrodes. The discontinuous shielding layer can be a second shield layer that is generally cylindrically disposed over an inner primary shielding layer. The primary and second shields both terminate at a location that is before the electrodes.

Other embodiments are directed to chronically implantable deep brain stimulation and MRI imaging probe systems. The systems include: (a) an MRI compatible elongate lead comprising an MRI antenna having an axially extending radially spaced apart first and second shield layer for internally receiving local in vivo MRI signals; (b) at least one electrode held on a distal portion of the lead and, in operation, configured to generate a stimulation pulse to deep brain neural tissue; (c) a stimulation circuit in communication with the at least one electrode; (d) a MRI signal receive circuit in communication with the MRI antenna; (e) a splitter circuit in communication with the stimulation and receive circuits for selectively electrically connecting either the MRI receive or stimulation circuit; and (f) means for inhibiting RF induced current on the second shield layer of the lead.

Still other embodiments are directed to MRI compatible deep brain stimulation and imaging probe systems. The systems include: (a) a flexible elongate probe body having opposing proximal and distal portions, the probe body comprising a plurality of electrodes disposed on the distal portion; (b) a plurality of axially extending conductors disposed in a core of the probe body, a respective one for each electrode; (c) an axially extending inner shield surrounding the plurality of conductors for at least a major portion of the length of the conductors; (d) an axially extending second shield radially spaced apart from the inner shield; (e) an axially extending first insulating/dielectric layer disposed intermediate of the inner and second shields; (f) an MRI antenna held by the probe body at the distal portion thereof, (g) an RF transmit decoupling circuit in communication with the MRI antenna; and (h) at least one connector attached to the proximal portion of the probe body, configured to hold a conductor transmission line for each of the electrodes.

Yet other embodiments are directed to medical kits. The kits include an elongate sterilized biocompatible and MRI compatible lead having opposing distal and proximal portions. The lead includes an MRI antenna, a plurality of stimulation electrodes on the distal portion, and a plurality of axially spaced apart RF chokes disposed in a shielding layer of the lead. The lead is configured to have selective operative first and second electrical transmission paths associated with first and second operational modes. The first transmission path connecting the MRI antenna with an MRI scanner and decoupling the electrodes during MRI operation and the second transmission path connecting the electrodes with a stimulation or recording source during electrical stimulation or recording.

Additional embodiments are directed to methods of placing and operating a deep brain stimulation probe. The methods include: (a) inserting a flexible elongate lead comprising an MRI antenna and at least one stimulation electrode on a distal portion thereof into a brain of a subject; (b) connecting the lead to an MRI scanner interface in communication with a splitter circuit having at least two different electric transmission paths, a first for MRI operation and a second for stimulation operation; (c) obtaining MRI signals associated with local neural tissue proximate the MRI antenna from the MRI antenna using the first transmission path; (d) placing the electrode on the lead at a desired location in the brain based on data from the obtaining step; then (e) stimulating neural tissue with the electrode using the second transmission path; and (f) configuring the lead to inhibit the formation and/or transmission of RF induced current. The stimulating and obtaining steps are carried out using the same lead.

Other embodiments are directed to computer program products for operating a multi-purpose MRI compatible stimulation probe with MRI antenna. The computer program product includes a computer readable storage medium having computer readable program code embodied in the medium. The computer-readable program code includes computer readable program code that controllably engages a desired operational mode of at least one of a plurality of different modes including a first or second operational mode for a MRI compatible stimulation probe with at least one electrode and an MRI antenna. The first operational mode having a first transmission path connecting the MRI antenna with an MRI scanner and decoupling the electrodes during MRI operation and the second operational mode having a second transmission path connecting the electrodes with a stimulation or recording source during electrical stimulation or recording.

The computer readable program code may be configured to time the selection of the second operational mode to occur proximate in time but after an MRI signal acquisition by the MRI antenna in the first operational mode. The computer readable program code may be configured to obtain microrecordings of local tissue in substantially real time proximate in time to an MRI signal acquisition by the MRI antenna in the first operational mode. The computer readable program code may be configured to obtain a plurality of MRI signals of local neural tissue proximate the MRI antenna in substantially real time, then obtain a plurality of microrecordings of the local neural tissue to allow a clinician to track placement of the probe using both MRI data and audio data.

Yet other embodiments are directed to an MRI compatible therapeutic stimulation probe that includes: (a) an elongate flexible probe body having an axially extending internal cavity disposed therein; (b) at least one electrode held by a distal portion of the probe body; and (c) at least one axially extending conductor configured to slidably extend into the cavity of the probe body, the at least one conductor having increased rigidity relative to the probe body. During positioning in a body, the at least one conductor cooperates with the probe body and defines an in vivo MRI antenna used to obtain MRI signals for MRI positional guidance. After placement, the at least one conductor can be removed from the probe body, leaving the probe body in position in the body.

A cannula may be configured to be inserted into a burr hole placed in a patient's skull and the stimulation probe and MRI antenna probe may be configured for deep brain placement guided through the cannula.

In some embodiments, the cannula is configured to cooperate with the MRI antenna probe to define an MRI receive antenna when the MRI antenna probe is held inside the cannula. In particular embodiments, the cannula comprises a conductive shielding layer that cooperates with the MRI antenna probe to define an MRI receive antenna during positioning in a body used to obtain MRI signals for MRI positional guidance of the stimulation electrode on the same probe.

These and other embodiments will be described further below.

BRIEF DESCRIPTION OF THE DRAWINGS

FIG. 5A is a partially exploded schematic illustration of a multi-purpose probe according to embodiments of the present invention.

FIG. 5B is a section view of the probe shown in FIG. 5A, illustrating the probe cavity without the center conductor(s).

FIG. 5C is a section view of the probe shown in FIG. 5A, illustrating the probe cavity holding the center conductor(s).

DETAILED DESCRIPTION OF EMBODIMENTS OF THE INVENTION

Figure 1:
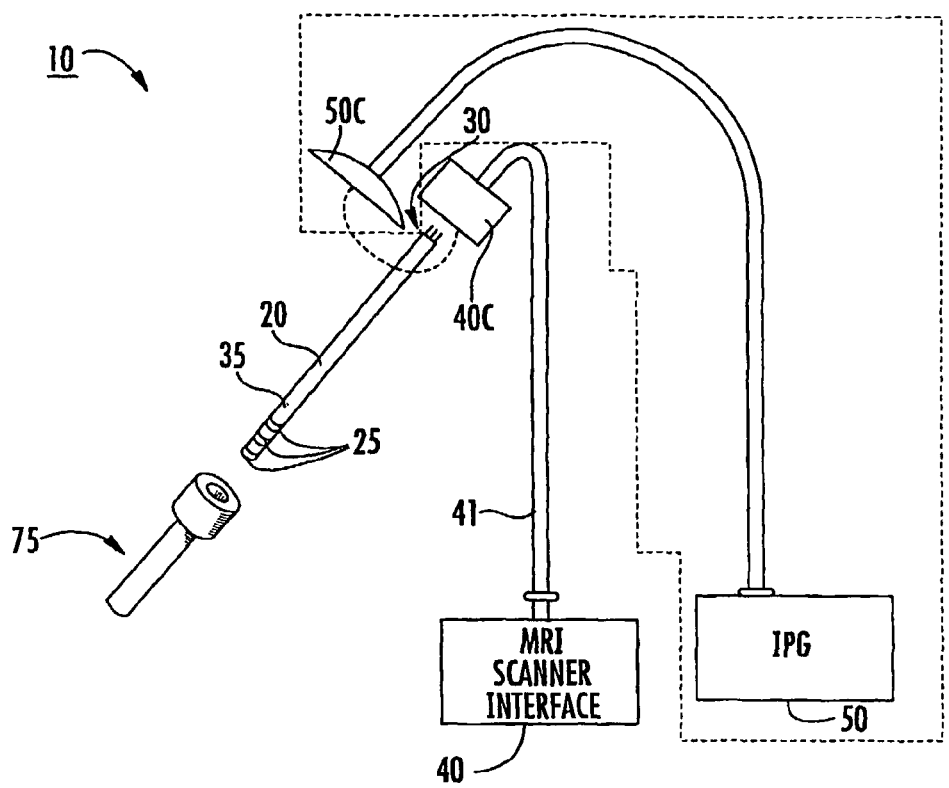
FIG. 1 is a schematic illustration of a medical kit with an implantable stimulation lead according to embodiments of the present invention.
Figure 2:
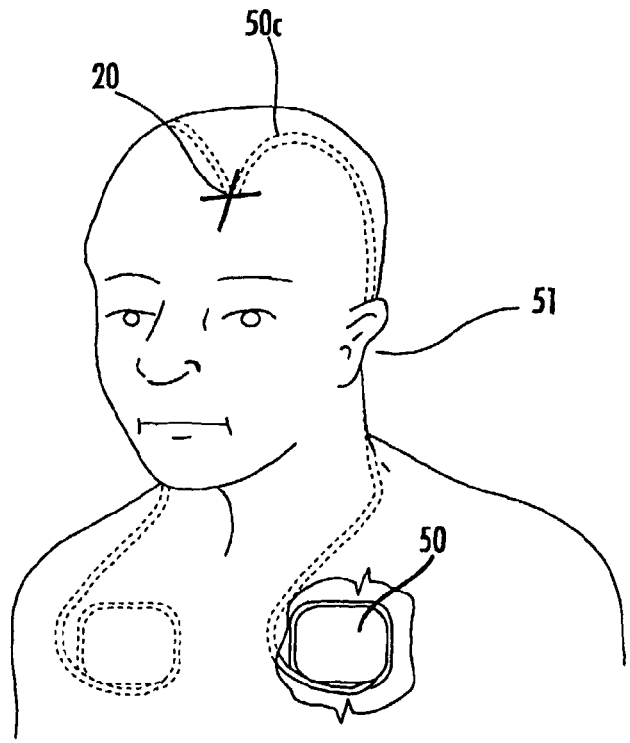
FIG. 2 is an image of a subject having implanted deep brain stimulation leads which are MRI compatible according to embodiments of the present invention.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain antenna embodiment, features or operation of one lead system embodiment can apply to others.

In the drawings, the thickness of lines, layers, features, components and/or regions may be exaggerated for clarity and broken lines illustrate optional features or operations, unless specified otherwise. In addition, the sequence of operations (or steps) is not limited to the order presented in the claims unless specifically indicated otherwise. It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and should not be interpreted in an idealized or overly formal sense unless expressly so defined herein.

Probe embodiments of the present invention can be configured to stimulate any desired internal region of the body or object. The object can be any object, and may be particularly suitable for animal and/or human subjects. Some probe embodiments can be sized and configured for brain stimulation, typically deep brain stimulation. Some probe embodiments can be configured to stimulate a desired region of the sympathetic nerve chain. Other embodiments may be directed to other anatomical structures, organs or features including deep tissue, lumens, and the like. For example, the probe systems of the present invention may be configured for treatment of cardiac, gastrointestinal, urinary, or other body regions.

Examples of known stimulation treatments and/or target body regions are described in U.S. Pat. Nos. 6,708,064; 6,438,423; 6,356,786; 6,526,318; 6,405,079; 6,167,311; 6539,263; 6,609,030 and 6,050,992, the contents of which are hereby incorporated by reference as if recited in full herein.

Figure 3A:
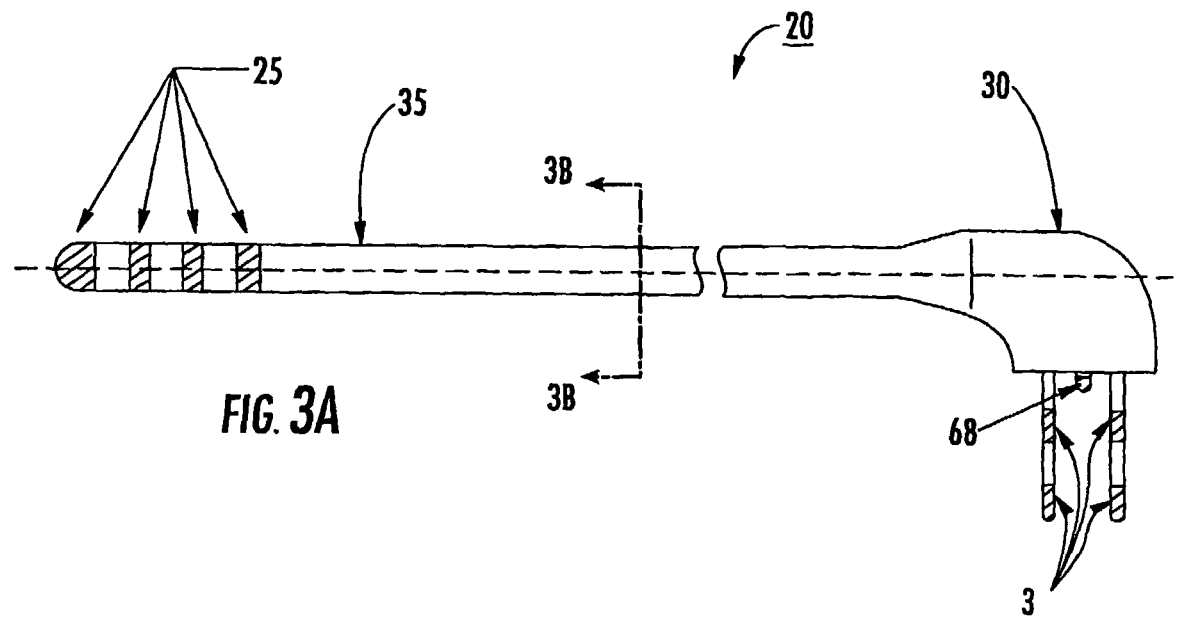
FIG. 3A is a side view of a stimulation lead according to embodiments of the present invention.
Figure 3B:
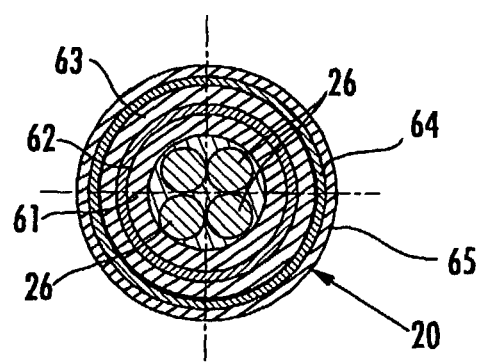
FIG. 3B is a section view of the device shown in FIG. 3A, taken along line 3B-3B.
Figure 3C:
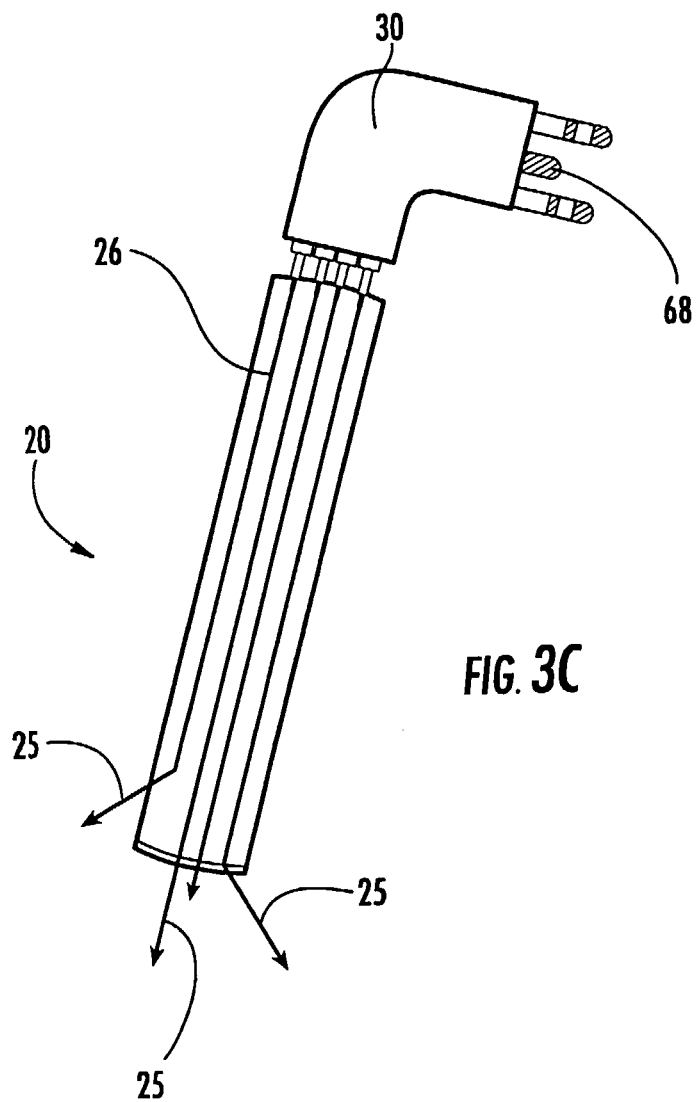
FIG. 3C is a side schematic view of a probe with linear and/or extendable electrodes according to embodiments of the present invention.

Embodiments of the present invention will now be described in detail below with reference to the figures. FIG. 1 illustrates a medical kit 10 that includes at least one stimulation lead or probe 20 with at least one stimulation and/or ablation electrode 25. The at least one electrode 25 is shown in FIG. 1 as three generally cylindrical, axially spaced apart electrodes. The terms "lead" and "probe" can be used interchangeably to indicate a body used to support the stimulation electrode(s) 25. Other numbers of electrodes as well as other electrode configurations can be used. FIG. 3A illustrates four electrodes 25 and FIG. 3C illustrates that the electrodes 25 may be generally linear electrodes 25 that can translate with respect to the body of the probe to extend out an end portion and/or sidewall portions thereof to provide additional (typically individually selectable) stimulation and/or sensing options. It is contemplated that the electrode(s) can be sized and configured to "fit" the desired internal target, which may be a relatively small region, such as less than about 1-3 mm. Typically, as shown in FIG. 1, the electrode(s) 25 can be held on a distal portion of the probe body. The connector 30 on the proximal end portion of the probe body can be configured to reside outside of the body during lead placement. The proximal portion of the probe body can be configured to releasably engage either an MRI scanner interface 40 or an implantable pulse generator 50 via respective connectors 40c, 50c.

As shown by the broken line, the kit 10 may optionally also include at least one implantable pulse generator 50 with an implantable lead 51 and a connector 50c. The generator and lead 50, 51 can also comprise MRI compatible materials and/or components. In addition, optionally, the kit 10 can include an MRI interface lead 41 and/or MRI scanner interface 40. The MRI interface 40 and/or lead 41 may be standard equipment useable across many procedures with different probes 20. The lead 41, connector 40c and/or MRI interface 40 may be provided as a single-use disposable sterilized component in the kit 10 or sterilized by the clinic between uses. The probe 20 is typically an elongate flexible probe comprising an outer layer of elastomeric material such as a polymer that extends across the outer surface of the probe body while leaving the electrode(s) 25 configured to contact the tissue in position in the body. The probe 20 includes at least one conductor lead 26 (FIG. 3B) that electrically connects the electrode 25 to a remote input or output source, such as either the MRI scanner interface 40 or implantable pulse generator 50. The lead(s) 26 can comprise any suitable material, and may, in some embodiments, comprise a shape memory alloy such as Nitinol. The connector 50c for the implantable pulse generator 50 may be configured with a smaller profile than that of the MRI lead connector 40c as it may be configured to be implanted under the skin of the subject for chronic stimulation.

As shown in FIG. 1, in some embodiments, the kit 10 may also include an MRI compatible generally rigid cannula 75 and/or a cannula 75 with increased rigidity relative to the probe that is configured to slidably receive at least the distal and intermediate portions of the probe body to guide the probe 20 into position. As with the interface lead 41, the cannula 75 can be single-use and disposable and provided as a sterilized component in the kit 75, or it may be re-used as a standard component and sterilized by the user/clinic. The cannula 75 can be configured according to a desired body entry location; e.g., for oral entry, the cannula 75 can be formed into a bite block, nasal cavity or ear plug member, and for non-neural uses, such as placement in the spinal column, no cannula may be required.

For MRI compatible uses, the cannula 75, the probe 20, the MRI interface cable 41 and connector 40c can comprise non-magnetic MRI compatible material(s) and be configured to operate in a high magnetic field environment. As noted above, in some embodiments, the implantable pulse generator 50 as well as the implantable lead 51 and connector 50c may also comprise MRI compatible materials to allow post-placement MRI interrogation of the subject.

Figure 4:
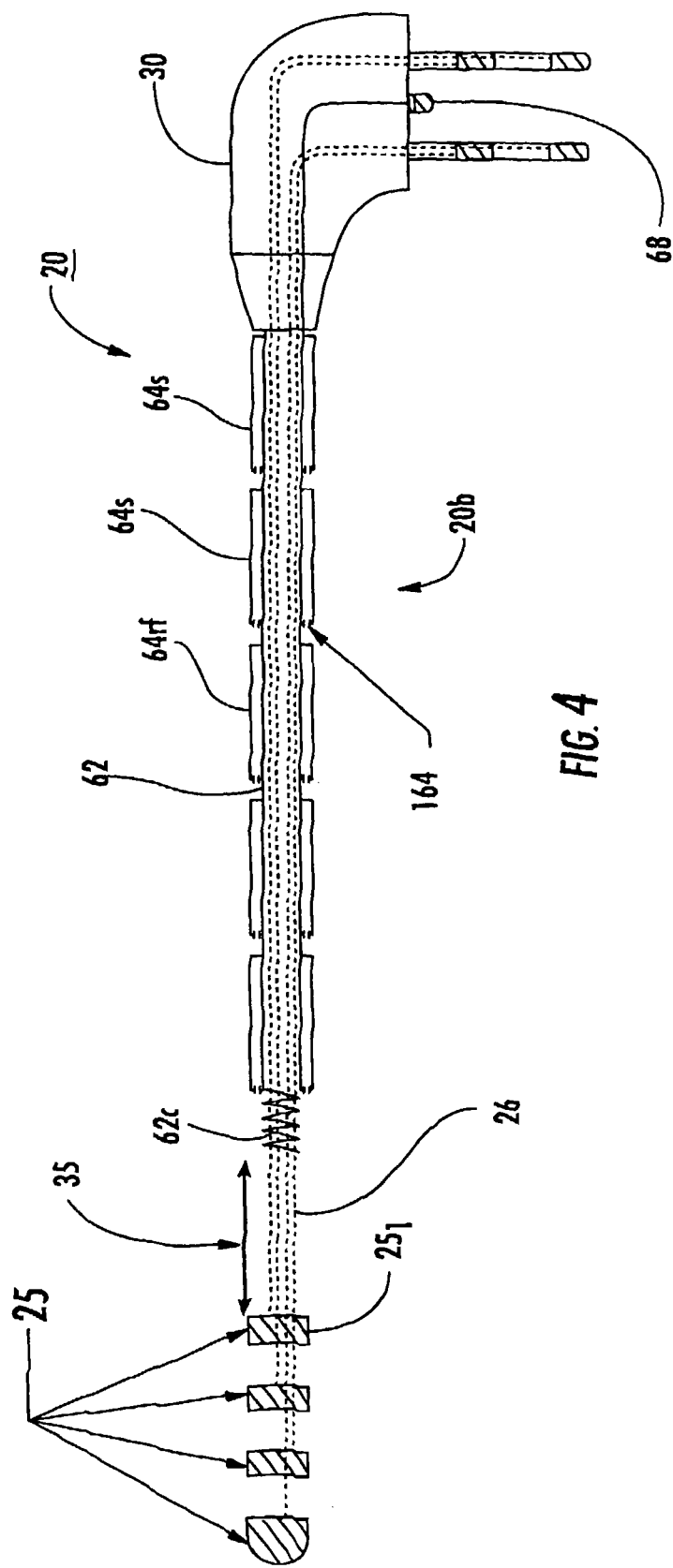
FIG. 4 is an electrical schematic diagram of the device shown in FIG. 3A according to embodiments of the present invention.

In some embodiments, the probe 20 comprises an MRI antenna 35 that is configured to pick-up MRI signals in local tissue during an MRI procedure. The MRI antenna 35 can be configured to reside on the distal portion of the probe 20. In some embodiments, the antenna 35 has a focal length or signal-receiving length of between about 1-5 cm, and typically is configured to have a viewing length to receive MRI signals from local tissue of between about 1-2.5 cm. The MRI antenna 35 is shown in FIGS. 3B and 4 as comprising a coaxial antenna. However, other antenna configurations can be used, such as, for example, a whip antenna, a coil antenna, a loopless antenna, and/or a looped antenna. See, e.g., U.S. Pat. Nos. 5,699,801; 5,928,145; 6,263,229; 6,606,513; 6,628,980; 6,284,971; 6,675,033; and 6,701,176, the contents of which are hereby incorporated by reference as if recited in full herein. See also U.S. Patent Application Publication Nos. US 2003/0050557; US 2004/0046557; and 2003/0028095, the contents of which are also hereby incorporated by reference as if recited in full herein.

FIGS. 3A-3B illustrate one embodiment of a probe 20 with a plurality of electrodes 25. At least one of the electrodes 25 can be a sensing electrode (i.e., micro-electric recording). Typically, one or more of the electrodes 25 may be able to both sense and stimulate (or ablate). For neural uses, different regions in the brain provide different sensed intensities, frequencies and/or pitches (typically readings of between about 1-4 microvolts) which are identifiable.

FIG. 3B illustrates that the core of the probe 20 can be configured to hold a plurality of axially extending conductors 26, typically a respective one for each electrode 25. In other embodiments, greater or lesser numbers of conductors than electrodes may be used. The conductors 26 may be static and held generally encapsulated in a first insulating dielectric layer 61. In other embodiments, the conductors 26 may be held in the first dielectric material 61 so that they can translate in the axial and/or generally outward or transverse directions as shown in FIG. 3C. Referring again to FIG. 3B, an axially extending first shielding layer 62 can surround the first dielectric layer 61. A second axially extending insulating dielectric layer 63 can surround the first shielding layer 62. A second axially extending shielding layer 64 can be electrically connected to the first shield layer 62 (that may also be called a primary shield layer) at a proximal end portion thereof. An outer polymeric insulator layer 65 can surround the inner layers 61-64 while terminating to typically expose the electrodes 25 to allow stronger stimulation contact during operation. The conductors 26 extend from the connector 30 to the respective electrode 25. The probe 20 includes an electrical ground 68 and the connector 30 connects the ground 68 and each electrode 25.

FIG. 4 illustrates an electrical schematic of the probe 20 shown in FIGS. 3A and 3B. As shown, the primary or first shield layer 62 axially terminates at a distal portion of the probe in advance of the first electrode $25_1$. The primary shielding 62 may be formed into a coil 62c at a distal portion of the probe 20. In other embodiments, the primary shielding 62 can terminate without coiling (not shown). In yet other embodiments, the shielding 62 may be coiled a distance past one or more electrodes 25, including all the way forward to the distal end portion (not shown). In some embodiments, a respective one conductor 26 can extend to a corresponding electrode 25, with the longest conductor 26 corresponding to the more distal electrode 25. The conductor(s) 26 may be substantially linear along the length in the probe body as shown, or may be coiled. If coiled, the coil for the conductor 26 may be at a distal portion, just before the respective electrode 25, which may increase signal (not shown).

Each electrode 25 is typically in communication with at least one of the insulated conductors 26. At the proximal end of the probe 20, the conductors 26 are connected to a connector 30 so as to be connected to the implantable signal generator 50 or to the interface circuit 40 during MRI guided probe/lead/cable placement. These insulated conductors 26 are typically covered with a polymeric insulator sleeve 61 and a conducting material is cylindrically layered to form the first shielding layer 62 over the insulator. This shielding 62 is terminated proximal to the electrodes and is not in electrical contact with the conductors or the electrodes. A second insulator/polymeric/dielectric layer 63 further insulates this shielding to form multi-core coaxial type cable system with an impedance that is typically between about 10-100 ohms. The RF chokes 64rf can be integrated or built into the shielding 64 in the form of a second shielding, which is not continuous and has multiple sections each λ/4 or less in length. As shown in FIG. 4, at the proximal end, each section or segment 64s is connected to the primary shielding 62, and the distal end may not be electrically connected to the primary shielding 62, or is connected with a capacitance 164 in between the primary and secondary shielding, 62, 64, respectively. A top insulator/polymeric layer 65 can be used to insulate the probe body 20b, except for the electrodes 25.

As shown by the axial arrow in FIG. 4, the MRI active portion of the antenna 35 may extend between a location where the primary shield 62 terminates and the first electrode $25_1$. However, as noted above, other antenna 35 configurations may also be used. As shown, the second shield layer 64 comprises a plurality of axially spaced apart RF chokes 64rf.

The term "RF chokes" refers to a shielding layer configuration that provides an electrical length of less than or equal to $\lambda/4$ (from the perspective of external electromagnetic waves) to inhibit the formation and/or propagation of RF induced current or standing waves in an AC (alternating current, e.g., diathermy applications) or RF exposure environment. The physical length that provides the electrical wavelength may vary depending on the materials used in fabricating the probe (such as dielectric constant) and the magnetic field in which it is used. In some embodiments, the probe 20 has a physical length that is greater than 10 cm, typically between about 20 cm to about 150 cm. In some embodiments, the implantable lead segment 50 can also include RF chokes 64rf formed along target regions or along substantially the entire implantable length. In the embodiment shown in FIG. 4, the RF chokes 64rf comprise a plurality of disconnects of the shield 64 and/or discrete electrically isolated second shield segments. In other embodiments, the RF chokes 64rf can include a series of axially spaced apart Balun circuits or other suitable circuit configurations. See, e.g., U.S. Pat. No. 6,284,971, the contents of which are hereby incorporated by reference as if recited in full herein, for additional description of RF inhibiting coaxial cable that can inhibit RF induced current.

As shown in FIG. 4, the second shield layer 64 may be coupled to the first shielding layer 62 at opposing ends of the segments 64s. As shown, one end (typically the proximal end portion) of the disconnected segment 64s is directly coupled to the shielding layer 62 and the other end (typically the distal end portion) is capacitively coupled to the first shielding layer 62. Each segment 64s may be configured to engage the first shield layer 62 in the same manner or in an opposing different electrical manner (not shown).

FIGS. 5A-5C illustrate another embodiment of a probe 20. In this embodiment, the probe body 20b is configured to define an axially extending cavity 27 (FIG. 5B) that is sized and configured at least one conductor 26 therein. FIG. 5B illustrates the probe body 20b without the conductor 26 with the cavity 27 open and FIG. 5C illustrates the conductor 26 in position. The conductor 26 can be a single conductor 26 as shown or a plurality of (typically structurally bound or bundled) conductors. The conductor 26 can be configured similar to a guidewire that can be released from the probe body 20 once the probe body is in position and/or can provide structural rigidity to the probe 20 during placement. As shown in FIG. 5C, in position, the conductor 26 can be configured to cooperate with the other components held on/in the probe 20 to define the MRI antenna 35 and to allow for MRI guidance. The probe 20 can provide a ground while the conductor 26 can provide the (+) electrical path. The conductor 26 can reside in the probe body during insertion or be extended through a distal end portion thereof. The conductor 26 can be packaged in position in the probe 20 or may be assembled on site. Instead of using the internal conductor(s) to connect the electrodes, the probe body 20b can include electrical conductive traces or wires 25t (typically subsurface and under an insulation layer 65) that connect the electrodes 25 to the input/output source(s). Although shown as having several dielectric and conductive shield layers in FIGS. 5B and 5C, other probe body configurations can be used to provide the desired electrode and/or MRI antennas.

The probe body cavity 27 and/or conductor 26 can be configured with matable structures that allows for angular adjustment in the cavity. For example, one outer perimeter portion of the conductor 26 may be planarized, flattened or roughened.

Although not shown, in some embodiments, the probe 20 can be configured with one or more lumens and exit ports that deliver desired cellular, biological, and/or drug therapeutics to the target area, such as the brain. The probe 20 may also incorporate biopsy and/or injection needles and/or ablation means.

Embodiments of the present invention provide a multi-function MRI safe lead or probe 20 that can operate at least bimodally: namely, during MRI procedures to obtain MRI signal from local tissue in vivo and to stimulate and/or ablate the target tissue during and/or after an MRI procedure. In some embodiments, the probe 20 is chronically implantable and can operate in at least three modes to: (1) selectively sense microelectric activity in local tissue, (2) stimulate local tissue, and (3) obtain MRI signals of local tissue. Each of the operations are typically performed serially or independently of the others. The probe 20 can be configured for use in any suitable MRI scanner, such as low field magnets (typically about 0.5-1.0 T fields), to a conventional 1.5 T magnet or higher, such as 2 T, 3 T or even higher. MRI scanners are well known to those of skill in the art and include, but are not limited to, SIEMENS and GE MRI systems.

Configuring a probe 20 to function both as an MRI antenna 35 and a stimulation probe may reduce the time needed to place the electrodes in the desired location, provide for increased accuracy in location and/or reduce the number of times a device is inserted into the brain or other target region.

Figure 6:
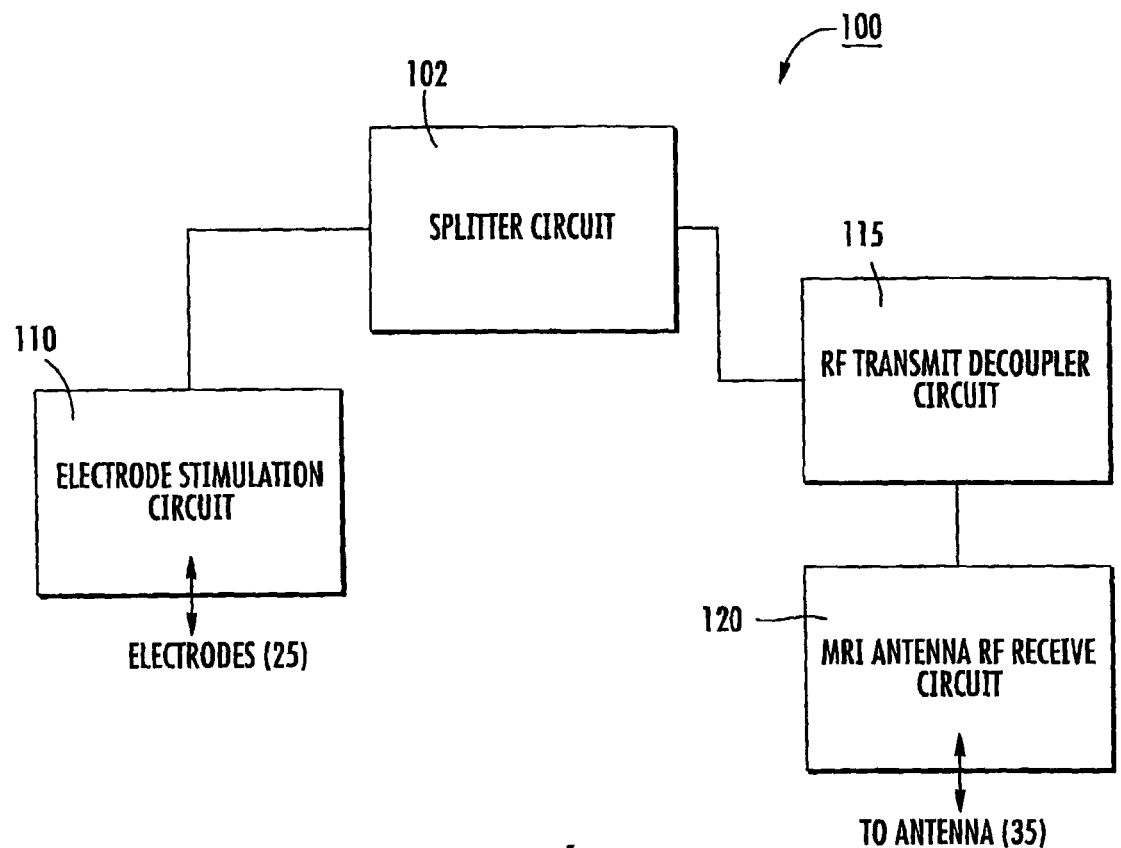
FIG. 6 is a block diagram of a bimodal lead operating circuit according to embodiments of the present invention.

FIG. 6 illustrates a circuit 100 that can provide the bimodal operation of the probe 20. As shown, the circuit 100 includes a splitter circuit 102 that is in communication with an electrode stimulation circuit 110 that provides the stimulation to the electrode(s) 25. The splitter circuit 102 is also in communication with an RF transmit decoupler circuit 115 that is in communication with an MRI antenna RF receive circuit 120 and the antenna 35. Certain components or all of the components can be held in the MRI scanner interface 40. In other embodiments, certain or all of the components of the circuit 100 can be held in the connector 30.

Generally stated, the interventional probe system can have a plurality of different operational modes such that the probe is associated with two or more operational transmission paths. In some embodiments, the probe can have two primary operational modes with different electric transmission paths, which are electrically directed using the splitter circuit 102. In operation, during an MRI procedure, an RF excitation pulse is transmitted to a subject. The MRI antenna is decoupled during RF transmission, then operative during a receive cycle to receive signal from local tissue. The stimulation electrodes 25 are typically isolated via the splitter circuit 102 so that only the MRI antenna 35 is active. The MRI interface 40 (FIG. 1) communicates with the MRI scanner and may be configured with a supplemental port to allow the implantable pulse generator to connect thereto, thereby allowing the IPG to stimulate the electrodes without decoupling the interface during the placement procedure (confirming proper placement). In some embodiments, the MRI interface 40 can include a stimulation and/or sensing mode that operates the electrodes independently of the IPG. In other embodiments, the connector 30 can be disconnected from the MRI interface after initial placement and connected to the IPG, and reconnected to the MRI interface 40 as desired for additional MRI data and/or images.

During MRI guided clinical implantation of the probe 20, the probe 20 can be used as an MRI antenna 35 to collect MRI or NMR data. Optionally, the probe 20 may be used to generate high-resolution images of the target internal anatomy (such as neural tissue) and/or to locate the position of the electrodes 25 in the body by obtaining MRI signals and (whether local signal or images). The MRI signal can be acquired by the external coils and/or internal MRI antenna 35.

The electrodes 25 can also be used to assess location via acquiring electrical signals from the target (neural) anatomy.

Figure 7A:
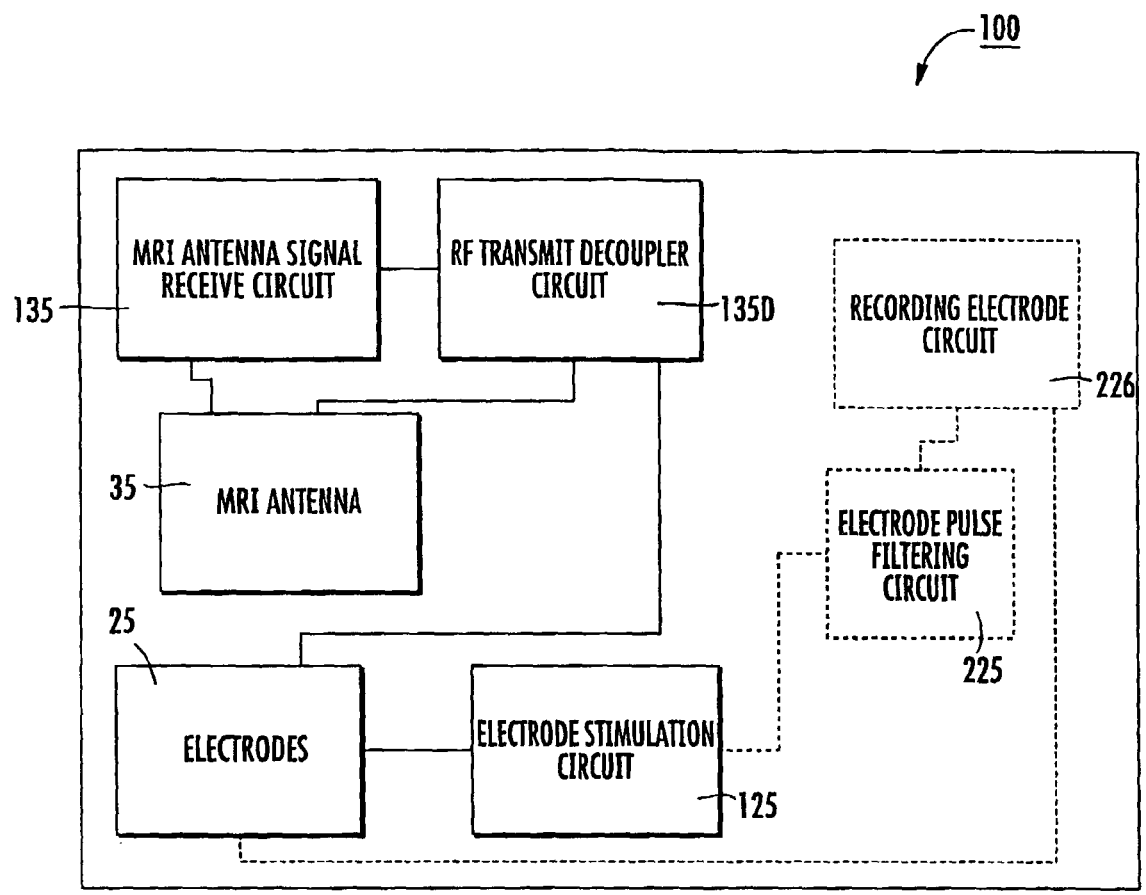
FIG. 7A is a block diagram of another operating circuit according to embodiments of the present invention.
Figure 7B:
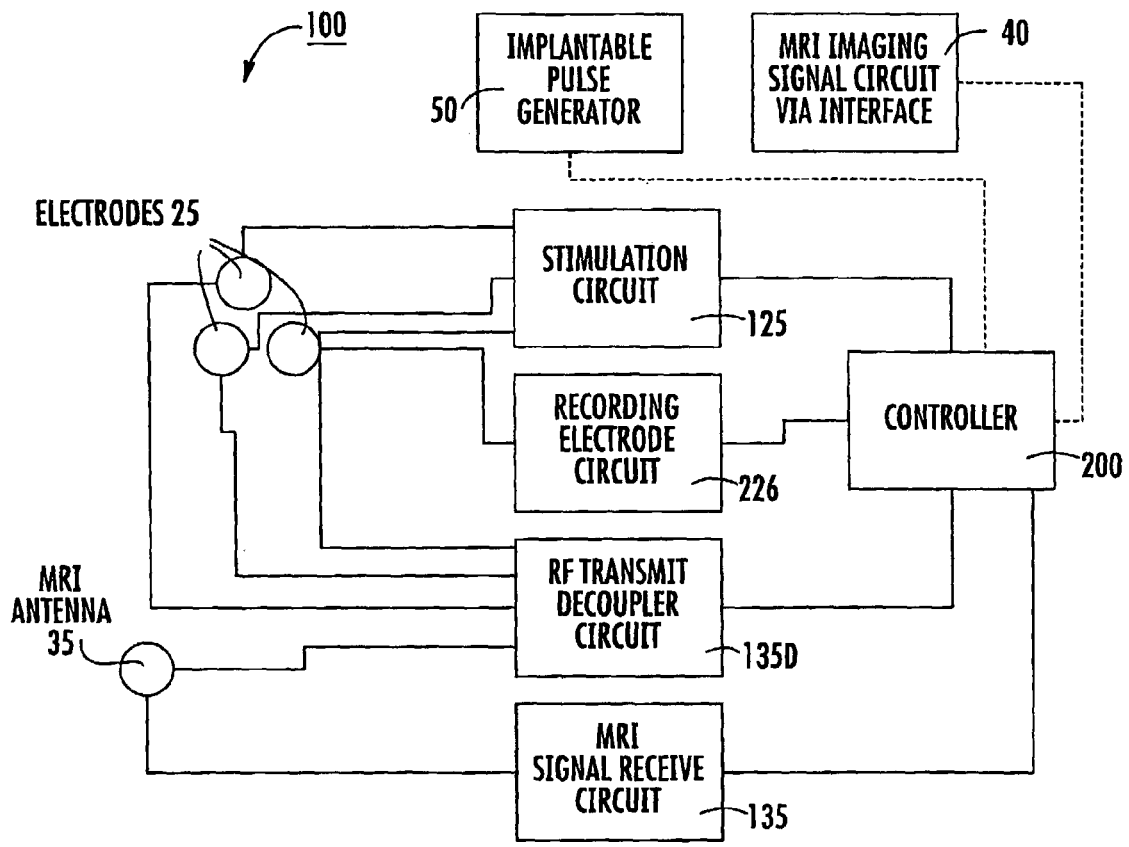
FIG. 7B is yet another block diagram of an operating circuit according to embodiments of the present invention.

FIGS. 7A and 7B illustrate different circuits 100 that may be used to provide the different operational modes of the probe 20. FIG. 7A illustrates an MRI antenna receive circuit 135 that receives the MRI responsive signal from local tissue and an RF transmit decoupler circuit 135D that can decouple the antenna 35 and the electrodes during RF transmission. The circuit 100 also includes an electrode stimulation circuit 125 that provides the stimulation pulses to the electrodes 25 and can include an electrode pulse filtering circuit 225 and a recording electrode circuit 226 used to gather local microelectric signals. FIG. 7B illustrates that the circuit 100 can include a controller 200, such as a digital signal processor, that can form part of the splitter circuit 102 (FIG. 6) to direct operation of the MRI antenna mode or the electrode mode.

Figure 8A:
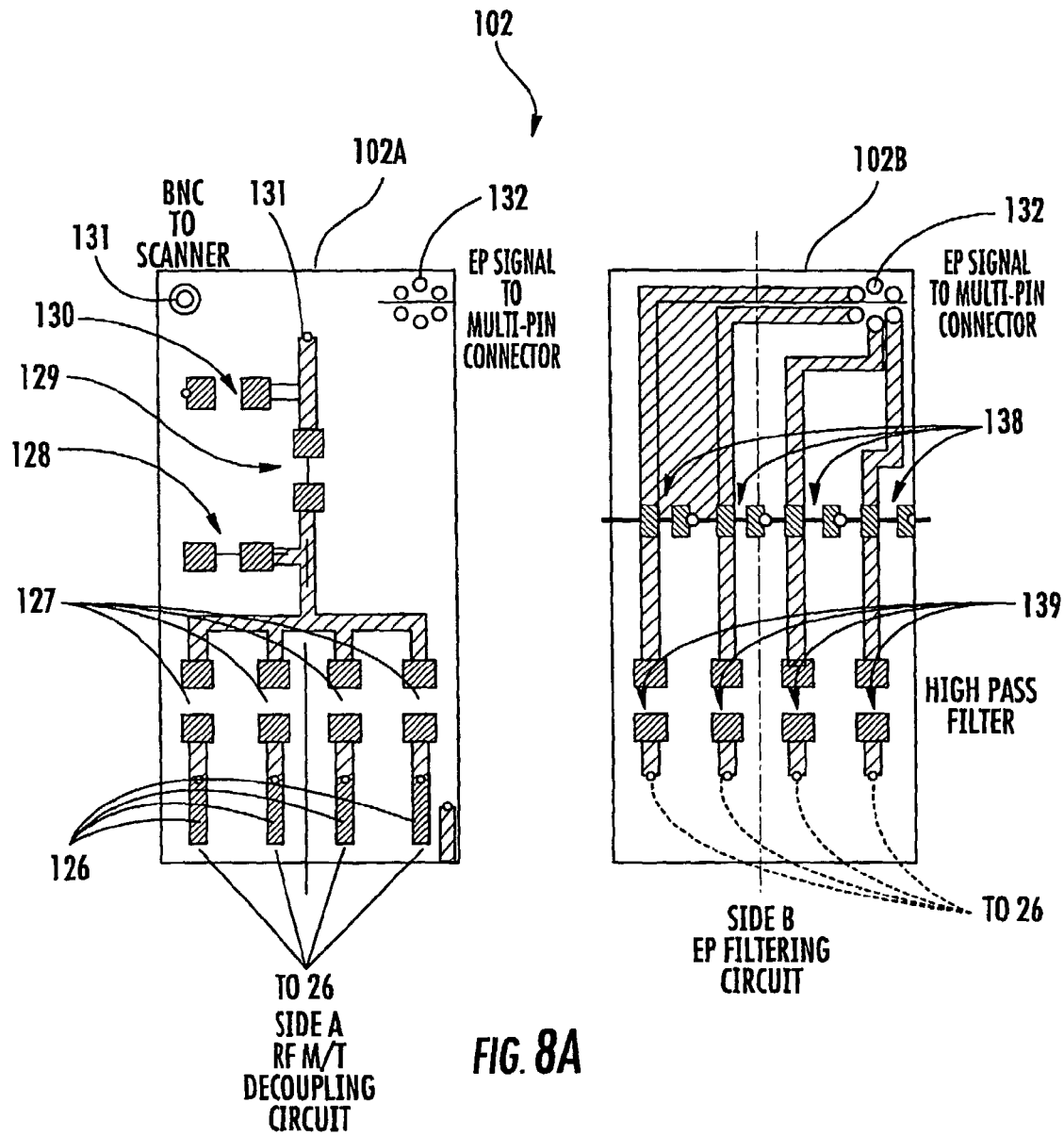
FIG. 8A is a schematic illustration of a splitter circuit according to embodiments of the present invention.
Figure 8B:
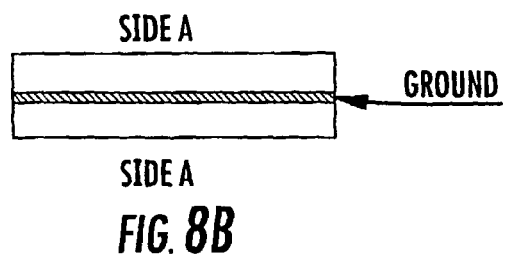
FIG. 8B is an end view of the circuit shown in FIG. 8A.

FIG. 8A is a schematic illustration of an exemplary splitter circuit 102 that provides different transmission paths for signals operating in the imaging (MR signal) mode and in the sensing microelectrical mode according to some embodiments of the present invention. FIG. 8A illustrates that the circuit 102 can have two sides, 102A, 102B, respectively that substantially overlie each other as shown in FIG. 8B with a ground plane therebetween. Side A 102A is the MRI antenna 35 active path with matching and tuning components including decoupling capacitors 127, conductor connections 126 (to respective conductors 26), an input (shown as a BNC input) to the MRI scanner 131, an input to a multi-pin connector for an electrode pulse signal 132 (EP signal) a PIN diode 128, a matching tuning inductor 129 and a matching/tuning circuit capacitor 130. Side B is the electrode operational circuit configured to act as a high pass filter. As shown, the respective electrical transmission paths to the conductors 26 include capacitors 138 (shown as 1000 pF capacitors) and 64 MHz RF blocking inductors 139. The blocking inductors 139 can be changed to block the frequency of the MRI system in use (higher frequencies for higher field magnets, i.e., for proton imaging, 96 MHz for 2 T, 128 MHz for 3 T). It is noted that components of the exemplary circuits are shown with respect to side A or B for ease of discussion, but certain of the circuits (or the entire circuit) may reside on a different side than that shown (and are not required to be on one side).

In some embodiments, the probe 20 can be placed in the brain, such as in the subthalamic nucleus or other deep brain target via a burr hole formed in the skull. MR imaging using the probe 20 can guide an increased accurate placement in the thalamus or other desired anatomies. Further, the electrical signals from the local tissue can be analyzed and evaluated to determine a final location of the electrodes 25. During this time, the probe can be connected to the MRI scanner interface 40 that can include a matching-tuning decoupling circuitry, and a splitter circuit to separate MR signal from the electrical signals generated by the local target tissue. Once the probe system is appropriately located in the desired anatomy, the stimulator can be connected for physiological confirmation of the function. If satisfactory, the proximal section of the probe can be routed subcutaneously and connected to the signal generator 50 implanted in the chest cavity. A telescopic system to lengthen or shorten the lead may be implemented in the proximal section of the probe, since diameter/profile may not be a significant concern in this region.

Figure 9:
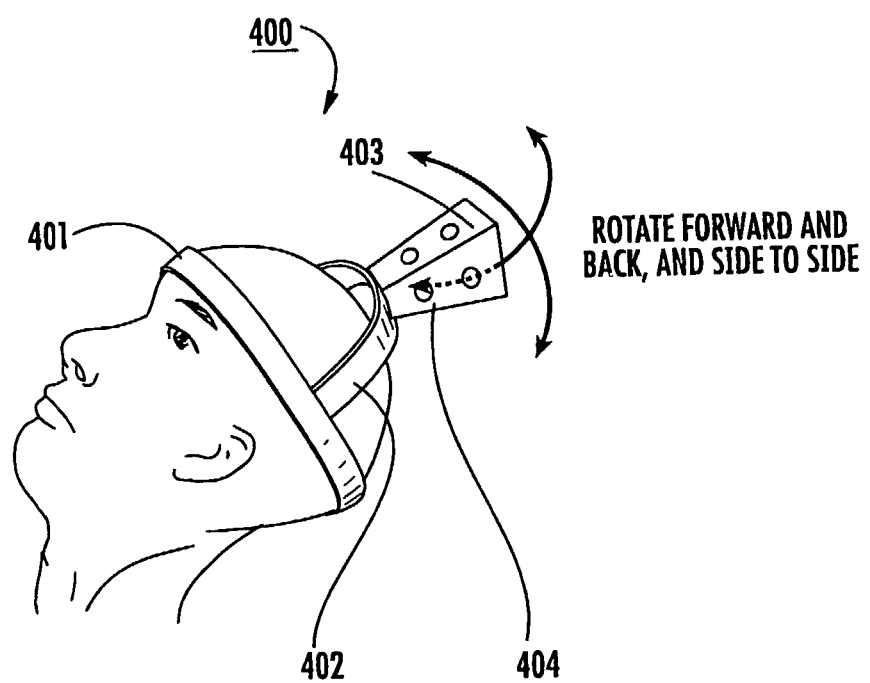
FIG. 9 is a schematic illustration of an MRI guidance fixture system configured to insert an MRI compatible stimulation probe into position according to embodiments of the present invention.

FIG. 9 schematically illustrates a stereotaxis guidance system 400 that can be used to implant the probes 20. Other guidance or implantation systems can also be used as will be known to those of skill in the art. In the embodiment shown, the system 400 comprises a generally circular ring 401 which is fixed to the patient's head. This ring 401 has one or more rotating semicircular rings 402 that are configured to advance the probe 20 in substantially straight trajectory. The ring 401 has a locator arm 403 which has MRI fiducial markers 404 to identify the long axis plane in which the probe 20 will be advanced into the brain. MR imaging is carried out to identify the location of the distal end of the probe 20. Once this is done a suitable long axis plane is identified and the locator/directing arm 403 is fixed in this plane. The probe 20 is used as an MRI antenna and tracked during advancing into the desired anatomy, collecting electrical signals generated by the cranial anatomy in substantially real-time. Once the distal electrodes are located in the appropriate anatomy the stereotaxis guidance system 400 is removed and the probe 20 remains in location as an implanted DBS lead.

The probe 20 may have one or more lumens configured to deliver cellular and/or biological therapeutics to the desired neural tissue. The lumens may receive extendable needles that may exit the probe from the distal end or from the sides, proximal, distal, or even, through the electrodes to precisely deliver cellular/biological therapeutics to the desired anatomy target. This delivery configuration may be a potential way to treat patients, where the cellular/biological therapeutics are delivered into the desired anatomy and the neurotransmitter/signal generator paces the cells to modify their function. In this way, even if the signal generator fails, the cells (stem cells) may differentiate and take over the function. MRI can be effectively used to monitor the efficacy of the therapy in the brain.

Figure 10A:
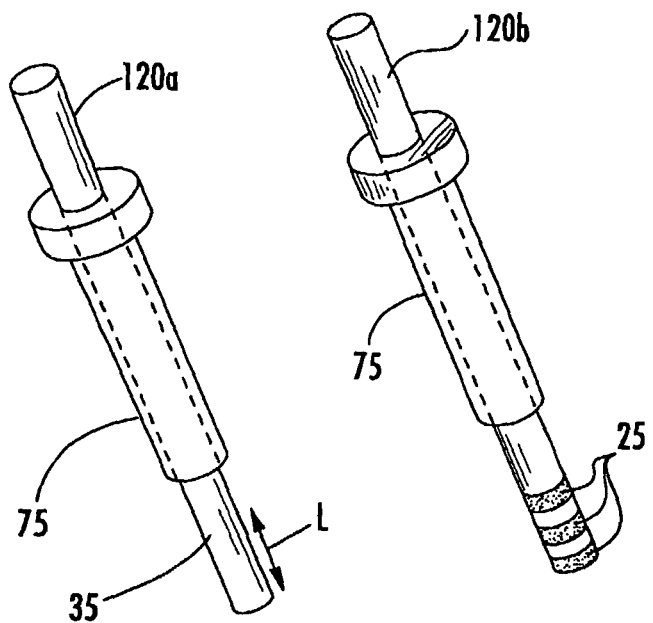
FIG. 10A is a schematic perspective illustration of a dual probe system according to other embodiments of the present invention.
Figure 10B:
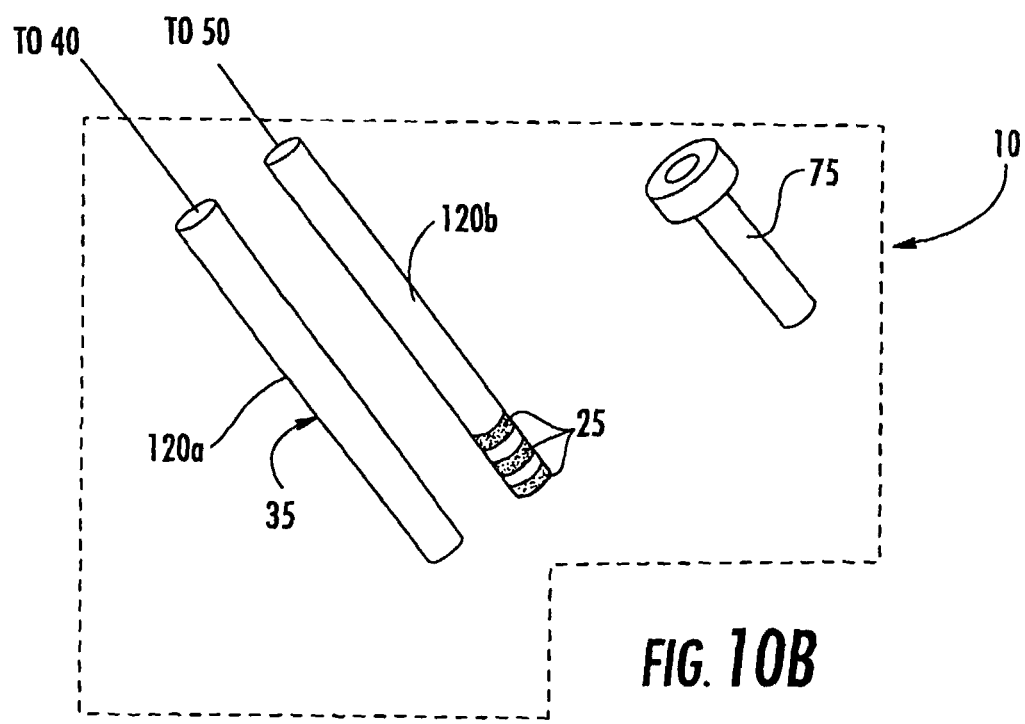
FIG. 10B is a schematic illustration of a dual probe kit according to embodiments of the present invention.

FIGS. 10A and 10B illustrate a dual probe system according to other embodiments of the present invention. In this embodiment, an MRI antenna probe 120a and a stimulation probe 120b can be sized and configured to serially enter a common cannula 75. The antenna probe 120a and the stimulation probe 120b can each include at least one sensing electrode. Each probe 120a, 120b can have a graduated scale or coordinate system that allows the antenna probe 120a to be used to obtain MRI imaging data used to locate the target in vivo location. The cannula 75 can include MRI fiducial markers (not shown). The antenna probe 120a can then be removed and replaced with the stimulation probe 120b that can be automatically advanced in the same trajectory to the same position based on the data provided by the antenna probe 120a and the controlled insertion to the location defined by the antenna probe 120a, typically to a high degree of precision. The two probes 120a, 120b can be sized and configured to have substantially the same cross-sectional area. In some embodiments, a non-conductive elastomeric sleeve (not shown), coating or other configuration can be used to size the probes 120a, 120b to snugly fit the cannula 75 as desired. In other embodiments, an insert can be used to adjust the size of the cannula 75 to correspond to that of the probe in use (also not shown). The cannula 75 and both probes 120a, 120b are MRI compatible and at least the probes 120a and 120b may include the RF chokes 64rf (FIG. 4).

In some embodiments, the antenna probe 35 can define a relatively small MRI receiver length "L," such as less than about 5 cm, typically between about 1-2.5 cm as noted above. As before, the antenna 35 can be any suitable type and is not limited to a coaxial cable type (including, for example, a dipole or loopless antenna as discussed above). The cannula 75 can form a shielding layer. In some embodiments, the cannula 75 may comprise a polymer and may include MRI compatible conductive material, such as Nitonal.

In some embodiments, the cannula 75 can be configured to cooperate with the antenna probe 120a to define an antenna 35. The cannula 75 can provide a ground and positive signal path. With reference again to FIG. 4, the cannula 75 can provide one or more insulating layers 61, 63 or shielding layers 62, 64 with the antenna probe 120a providing at least one conductor 26 and potentially one or more of the insulating layer 61 or shielding layers 62, 64. In particular embodiments, the cannula 75 provides the secondary shield layer 64 and may include RF chokes 64rf.

FIG. 10B illustrates that a kit 10' can comprise the two probes 120a, 120b and, optionally, the cannula 75. The antenna probe 120a can be configured to connect with the MRI interface 40 (FIG. 1) while the stimulation probe 120b can be configured to connect to the implantable pulse generator 50, each of which (along with respective leads 41, 51) may also form part of the medical kit 10'.

Figure 11:
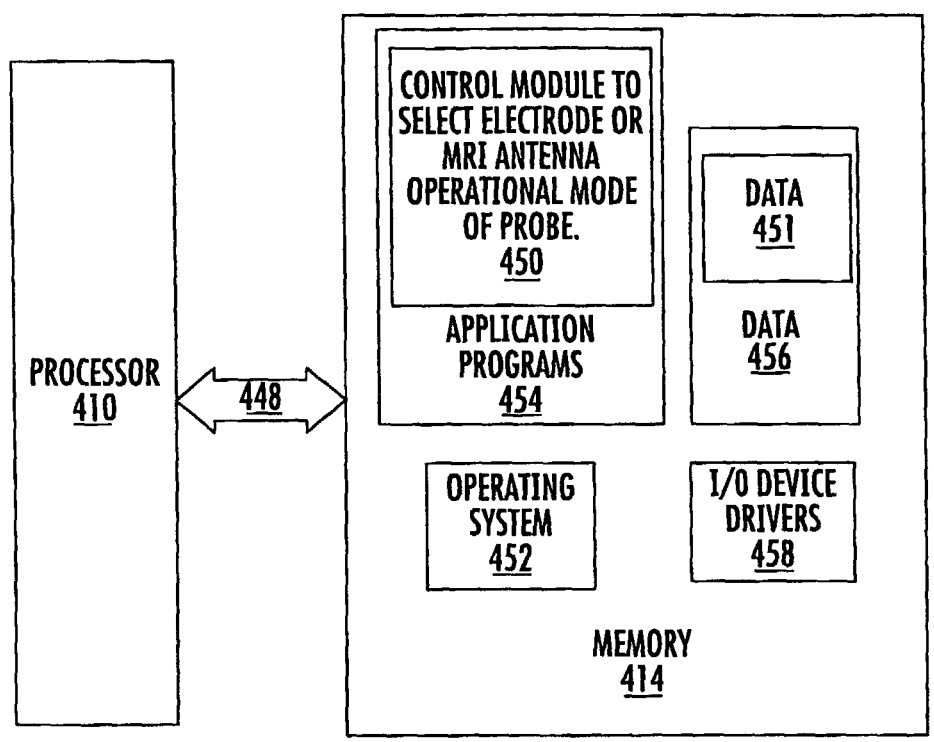
FIG. 11 is a block diagram of a data processing system according to embodiments of the present invention.

FIG. 11 is a block diagram of exemplary embodiments of data processing systems that illustrates systems, methods, and computer program products in accordance with embodiments of the present invention. The data processing systems may be incorporated in a digital signal processor in either the implantable pulse generator 50 and/or MRI scanner interface 40 and/or be in communication therewith. The processor 410 communicates with the memory 414 via an address/data bus 448. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

As shown in FIG. 11, the memory 414 may include several categories of software and data used in the data processing system: the operating system 452; the application programs 454; the input/output (I/O) device drivers 458; the MRI Antenna operation or Electrode Operation Module 450; and data 456.

As will be appreciated by those of skill in the art, the operating system 452 may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000 or other Windows versions from Microsoft Corporation, Redmond, Wash., Unix or Linux or FreeBSD, Palm OS from Palm, Inc., Mac OS from Apple Computer, LabView, or proprietary operating systems. The I/O device drivers 458 typically include software routines accessed through the operating system 452 by the application programs 454 to communicate with devices such as I/O data port(s), data storage 456 and certain memory 414 components. The application programs 454 are illustrative of the programs that implement the various features of the data processing system and can include at least one application, which supports operations according to embodiments of the present invention. Finally, the data 456 represents the static and dynamic data used by the application programs 454, the operating system 452, the I/O device drivers 458, and other software programs that may reside in the memory 414.

While the present invention is illustrated, for example, with reference to the Module 450 being an application program in FIG. 11, as will be appreciated by those of skill in the art, other configurations may also be utilized while still benefiting from the teachings of the present invention. For example, the Module 450 may also be incorporated into the operating system 452, the I/O device drivers 458 or other such logical division of the data processing system. Thus, the present invention should not be construed as limited to the configuration of FIG. 11 which is intended to encompass any configuration capable of carrying out the operations described herein. Further, the Module 450 can communicate with other components, such as an MRI scanner.

The I/O data port can be used to transfer information between the data processing system, the product pusher, and the clipper mechanism or another computer system or a network (e.g., the Internet) or to other devices controlled by the processor. These components may be conventional components such as those used in many conventional data processing systems, which may be configured in accordance with the present invention to operate as described herein.

The computer-readable program code can include computer readable program code that controllably engages a first or second operational mode for a MRI compatible stimulation probe with at least one electrode and an MRI antenna. The first operational mode having a first transmission path connecting the MRI antenna with an MRI scanner and decoupling the electrodes during MRI operation and the second operational mode having a second transmission path connecting the electrodes with a stimulation or recording source during electrical stimulation or recording.

The computer readable program code may be configured to time the selection of the second operational mode to occur proximate in time but after an MRI signal acquisition by the MRI antenna in the first operational mode. The computer readable program code may be configured to obtain microrecordings of local tissue in substantially real time proximate in time to an MRI signal acquisition by the MRI antenna in the first operational mode. The computer readable program code may be configured to obtain a plurality of MRI signals of local neural tissue proximate the MRI antenna in substantially real time, then obtain a plurality of microrecordings of the local neural tissue to allow a clinician to track placement of the probe using both MRI data and audio data.

The flowcharts and block diagrams of certain of the figures herein illustrate the architecture, functionality, and operation of possible implementations of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modi- That which is claimed is:

1. An in vivo medical stimulation probe, comprising:
an elongate lead having a length and at least one stimulation electrode disposed on a distal portion thereof, at least one axially exending conductor coupled to the at least one stimulation electrode, and an axially extending shielding layer surrounding the at least one conductor over at least a major length of the lead and terminating at a lead location that is in advance of the at least one stimulation electrode;
a plurality of RF chokes axially spaced apart along the length of the lead and disposed on and/or in the shielding layer in advance of the at least one electrode to inhibit induced RF current from forming and/or traveling along the shielding layer; and
an MRI antenna that is configured to collect and transmit signal data in response to an applied RF excitation pulse in an MRI scanner system, wherein the lead is MRI-compatible.

2. A medical stimulation probe according to claim 1, the lead further comprising a recording/sensing electrode disposed at the distal portion.

3. A medical stimulation probe according to claim 1, wherein the lead is a flexible lead, and wherein, the at least one stimulation electrode is a plurality of spaced apart stimulation electrodes and the at least one axially extending conductor is a plurality of conductors held in a core of the lead, a respective one for each electrode, and wherein the shielding layer is discontinuous and is configured to surround the conductors over at least a major length of the lead and terminate at a lead location that is in advance of the electrodes.

4. A medical stimulation probe according to claim 3, further comprising an axially extending primary inner shielding layer surrounding the core with the plurality of electrodes, wherein the discontinuous shielding layer is a second shielding layer that is generally cylindrically disposed over the primary inner shielding layer, and wherein the primary inner and second shielding layers both terminate at a distal location of the lead that precedes the electrodes.

5. A medical stimulation probe according to claim 4, further comprising a first insulating dielectric layer disposed between the conductors and the primary inner shielding layer, and a second insulting dielectric layer disposed between the primary inner shielding layer and the second shielding layer, wherein the conductors, the first and second insulating dielectric layers and the primary inner and second shielding layers comprise MRI compatible materials, and wherein the RF chokes are formed in the second shielding layer to provide an electrical length that is about $\lambda/4$ or less, wherein $\lambda$ is an MRI wavelength.

6. A medical stimulation probe according to claim 5, the lead further comprising a bio- and MRI-compatible outer polymeric layer.

7. A medical stimulation probe according to claim 1, wherein the MRI antenna is a coaxial antenna having a signal receiving length of between about 1-4 cm.

8. A medical stimulation probe according to claim 1, wherein the lead is chronically implantable, and wherein the at least one electrode is a plurality of electrodes that are sized and configured to apply deep brain stimulation.

9. A medical stimulation probe according to claim 8, wherein the lead has a length that is greater than 10 cm.

10. A medical stimulation probe according to claim 1, further comprising a connector disposed at a proximal end portion of the probe, the connector configured to releasably serially attach to both an implantable pulse generator and an MRI scanner interface, thereby allowing bimodal operation of the lead.

11. A medical stimulation probe according to claim 1, wherein the lead is configured to have at least two operational modes, including a first MRI operational mode wherein the lead receives MRI signals from the MRI antenna and a second therapeutic operational mode wherein the lead delivers a stimulation pulse to the at least one electrode.

12. A medical stimulation probe according to claim 11, wherein the at least one electrode is a plurality of electrodes, at least one of which is configured as a recording/sensing electrode, and wherein the lead is configured to provide trimodal operation with a third operational mode wherein the lead receives micro-electrical signals from local tissue from the recording/sensing electrode.

13. A medical stimulation probe according to claim 11, wherein the MRI antenna is configured to receive signal from local tissue over about a distance of about 2.5 cm or less.

14. A medical stimulation probe according to claim 13, wherein the MRI antenna is axially spaced apart from a closest one of the at least one electrode a distance of about 1-4 cm.

15. A chronically implantable deep brain stimulation and MRI imaging probe system, comprising:
the in vivo medical stimulation probe of claim 1, wherein the MRI antenna has axially extending, radially spaced apart first and second shielding layers, wherein the second shielding layer corresponds to the axially extending shielding layer of the in vivo medical stimulation probe;
a stimulation circuit in communication with the at least one stimulation electrode;
a MRI signal receiver circuit in communication with the MRI antenna; and
a splitter circuit in communication with the stimulation and receiver circuits for electrically connecting either the MRI receive or stimulation circuit.

16. A deep brain stimulation and MRI imaging probe according to claim 15, further comprising a decoupling circuit to electrically decouple the MRI antenna during an MRI RF transmit operation.

17. A deep brain stimulation and MRI imaging probe according to claim 15, further comprising a plurality of axially spaced apart discontinuities in the second shielding layer.

18. A deep brain stimulation and MRI imaging probe according to claim 15, wherein the RF chokes comprise balun circuits.

19. A deep brain stimulation and imaging probe according to claim 15, further comprising a microrecording electrode for receiving microelectric signals associated with neural tissue.

20. A deep brain stimulation and imaging probe according to claim 15, wherein the lead of the in vivo medical stimulation probe merges into a connector at a proximal portion thereof, the connector configured to serially interchangeably engage an MRI scanner interface and an implantable pulse generator.

21. An MRI compatible deep brain stimulation, and MRI signal acquiring probe system comprising:
the in vivo medical stimulation probe of claim 1, wherein the at least one stimulation electrode comprises a plurality of electrodes disposed on the distal portion of the lead of the in vivo medical stimulation probe and the at least one axially extending conductor comprises a. plurality of axially extending conductors disposed in a core of the probe, a respective one of the conductors associated with each electrode, wherein the axially extending shielding layer of the in vivo medical stimulation probe comprises an axially extending inner shield surrounding the plurality of conductors for at least a major portion of the length of the conductors;

an axially extending second shield radially spaced apart above the inner shield;

an axially extending first insulating/dielectric layer disposed intermediate of the inner and second shields;

an RF transmit decoupling circuit in communication with the MRI antenna; and at least one connector attached to the proximal portion of the probe body, configured to hold a conductor transmission line for each of the electrodes.

22. A system according to claim 21, wherein the connector is configured to attach to an MRI scanner having a splitter circuit for selectively operating the electrodes or the MRI antenna.

23. A system according to claim 21, further comprising an MRI interface that holds the RF transmit decoupling circuit, the MRI interface configured to connect the lead to an MRI scanner with the RF transmit decoupling circuit decoupling the MRI antenna during an MRI RF excitation transmission.

24. A system according to claim 23, wherein the RF transmit decoupling circuit comprises a matching and tuning decoupling circuit that engages an MRI scanner and decouples the electrodes.

25. A system according to claim 24, wherein the lead is configured to serially engage with an MRI scanner and an implantable pulse generator.

26. A system according to claim 25, wherein the implantable pulse generator is MRI-compatible.

27. A system according to claim 24, wherein the lead comprises at least one lumen and associated port configured to emit a therapeutic fluid to neural tissue.

28. A system according to claim 24, wherein the lead is configured to slidably enter a cannula with the connector held outside the cannula during deep brain placement.

29. A system according to claim 28, wherein the cannula is MRI-compatible.

30. A system according to claim 28, wherein the system is configured to operate with an MRI-compatible stereotactic guidance system during deep brain placement.

31. A system according to claim 21, wherein the RF transmit decoupling circuits is held the connector.

32. A system according to claim 21, further comprising a stimulation circuit coupled to the electrodes and a splitter circuit in communication with the RF transmit decoupling circuit and the stimulation circuit.

33. A system according to claim 32, wherein the stimulation circuit comprises a high pass filter disposed in a transmission path intermediate a stimulation source and the electrodes.

34. A system according to claim 33, wherein the stimulation circuit is configured to block RF signals at a resonant frequency associated with a magnetic field strength of a MRI system used to operate the MRI antenna.

35. A system according to claim 21, further comprising a splitter circuit having selective operative first and second electrical transmission paths associated with first and second operational modes, the first transmission path connecting the MRI antenna with the MRI scanner and decoupling the electrodes during MRI operation and the second transmission path connecting the electrodes with a stimulation or recording source during electrical stimulation or recording, respectively.

36. A system according to claim 35, wherein the splitter circuit is configured to act as a high pass filter during MRI operation to electrically isolate the second transmission path from the first transmission path.

37. A system according to claim 35, wherein the splitter circuit is held in an MRI interface that is releaseably attachable to the connector.

38. A system according to claim 37, wherein the splitter circuit is held in the connector.

39. A medical kit, comprising:
the in vivo medical stimulation probe of claim 1, the lead configured to have selective operative first and second electrical transmission paths associated with at least first and second operational modes, the first transmission path connecting the MRI antenna with an MRI scanner and decoupling the at least one stimulation electrode during MRI operation and the second transmission path connecting the at least one stimulation electrode with a stimulation, ablation or recording source during electrical stimulation, ablation or recording, respectively.

40. A medical kit according to claim 39, wherein the lead is configured and sized to be chronically implantable for deep brain stimulation.

41. A medical kit according to claim 39, wherein the lead comprises a connector at a proximal end portion thereof, the connector configured to engage a chronically implantable pulse generator in the second operational mode.

42. A medical kit according to claim 39, wherein the connector is configured to be in communication with an MRI scanner in the first operational mode.

43. A medical kit according to claim 42, wherein the connector is configured to connect to an MRI interface with a splitter circuit and RF transmit decoupler circuit with the MRI interface connecting to the MRI scanner.

44. A method of placing and operating a deep brain stimulation probe, comprising:
inserting the in vivo stimulation probe of claim 1 into a brain of a subject;
connecting the lead to an MRI scanner interface in communication with a splitter circuit having a first electric transmission path for MRI operation and a second electric transmission path for stimulation operation;
obtaining MRI signals associated with local neural tissue proximate the MRI antenna from the MRI antenna using the first transmission path;
placing the at least one electrode on the lead at a desired location in the brain based on the obtaining step;
then stimulating neural tissue with the at least one electrode using the second transmission path; and
configuring the lead to inhibit the formation and/or transmission of RF induced current, wherein, the stimulating and obtaining steps are carried out using the same lead.

45. A method according to claim 44, further comprising;
implanting the lead in the brain with the at least one electrode held at the desired location in the brain;
connecting the lead to an implantable pulse generator; and
stimulating the neural tissue with the at least one electrode based on a stimulation signal transmitted from the implantable pulse generator to provide a therapeutic treatment.

46. A method according to claim 44, wherein the placing step comprises inserting the lead through a bore of a MRI-compatible cannula body having increased rigidity relative to the lead, the cannula body extending through the skull into neural tissue.

47. A method according to claim 44, wherein the placing step is carried out using a sterotaxis guidance system with MRI fiducial markers.

48. A method according to claim 44, wherein the obtaining step is repeated and carried out in substantially real-time to track the location of the lead in the brain.

49. A method according to claim 44, wherein the lead comprises an axially extending lumen with at least one exit port, the method further comprising releasing a therapeutic fluid into the brain.

50. A method according to claim 44, wherein the obtaining step is repeated a plurality of times before the placing step, the method further comprising recording microelectric audio signals sensed from the at least one electrode and transmitting the audio signals to an external audio device intermediate at least some of the obtaining steps.

51. A method according to claim 50, wherein the MRI antenna and at least one electrode are decoupled during RF transmission in an MRI imaging session.

52. A method according to claim 44, wherein the at least one electrode is a plurality of electrodes, at least one of which is both a recording and stimulation electrode, and wherein the MRI antenna has a viewing length of between about 1-4 cm.

53. A method according to claim 44, further comprising splitting the operation of the lead into an MRI operation and a stimulation operation, wherein the at least one electrode has an electrical circuit transmission path that is different during stimulation and MRI operation.

54. A method according to claim 44, wherein the at least one electrode is a plurality of electrodes-and the method further comprises selectively attaching the connector to an MRI system or to an implantable pulse generator, depending on a desired operational mode.

55. A probe system, comprising:
an MRI compatible cannula having an axially extending bore; and
the in vivo medical stimulation probe of claim 1;
wherein the probe is configured to slidably extend through the cannula bore and wherein, in operation, the cannula and probe cooperate to define componentsf the MRI antenna.

56. A probe system according to claim 55, wherein the cannula is configured to be inserted into a burr hole placed in a patient's skull, and wherein the probe is configured for deep brain placement.

57. A probe system according to claim 55, wherein the cannula comprises a plurality of generally concentric tubular members configured to define axially extending shielding layer disposed over an inner conductive core, with the shielding layer and core being insulated from each other.

58. A probe system according to claim 55, wherein the cannula comprises a conductive shielding layer that cooperates with the probe to define the MRI antenna during positioning to obtain MRI signals for MRI positional guidance.

59. A probe system according to claim 58, wherein the probe is configured to remain implanted in the body.

60. A system according to claim 55, the system further comprising a controlled placement system that is configured to determine the positional location of the probe when held at a target region in the brain.

61. An MRI compatible therapeutic stimulation probe comprising:
an elongate flexible probe body having an axially extending internal cavity disposed therein;
at least one electrode held by a distal portion of the probe body;
at least one conductive trace or wire disposed within the probe body and coupled to the at least one electrode and configured and arranged to conductively connect the at least one electrode to a source; and
at least one axially extending conductor, separate from the at least one conductive trace or wire, configured to slidably extend into the cavity of the probe body, the at least one conductor having increased rigidity relative to the probe body,
wherein, during positioning in a body, the at least one conductor cooperates with the probe body and defines an in vivo MRI antenna used to obtain MRI signals for MRI positional guidance, and wherein, after placement, the at least one conductor can be removed from the probe body, leaving the probe body and electrode in position in the body.

62. An MRI probe according to claim 61, wherein the at least one electrode is a plurality of electrodes, at least one of which configured as a sensing and stimulation electrode.

63. An MRI probe according to claim 62, wherein the at least one conductor is a plurality of attached insulated conductors.

64. An MRI probe according to claim 61, wherein the probe body comprises a shielding layer with a plurality of axially spaced apart RF chokes.

65. An MRI probe according to claim 64, wherein the probe body comprises a first insulating layer, a first shielding layer, a second insulating layer and a second shielding layer, and wherein the RF chokes are disposed in the second shielding layer.

* * * * *